(12) United States Patent
Sasges et al.

(10) Patent No.: US 8,766,211 B2
(45) Date of Patent: Jul. 1, 2014

(54) FLUID TREATMENT SYSTEM

(75) Inventors: Michael Sasges, Victoria (CA); Jim Fraser, St. Thomas (CA)

(73) Assignee: Trojan Technologies (CA)

( * ) Notice: Subject to any disclaimer, the term of this patent is extended or adjusted under 35 U.S.C. 154(b) by 0 days.

(21) Appl. No.: 13/054,701

(22) PCT Filed: Jul. 15, 2009

(86) PCT No.: PCT/CA2009/000977
§ 371 (c)(1),
(2), (4) Date: Apr. 8, 2011

(87) PCT Pub. No.: WO2010/006428
PCT Pub. Date: Jan. 21, 2010

(65) Prior Publication Data
US 2011/0180723 A1 Jul. 28, 2011

Related U.S. Application Data

(60) Provisional application No. 61/129,732, filed on Jul. 15, 2008.

(51) Int. Cl.
*A61L 2/10* (2006.01)

(52) U.S. Cl.
USPC ..... 250/436; 250/437; 250/432 R; 250/504 R

(58) Field of Classification Search
None
See application file for complete search history.

(56) References Cited

U.S. PATENT DOCUMENTS 5,597,482 A * 1/1997 Melyon ........................ 210/209
7,169,311 B2 * 1/2007 Saccomanno ............... 210/198.1
7,408,174 B2 * 8/2008 From et al. .................... 250/436
7,507,973 B2 * 3/2009 Bircher ....................... 250/455.11
7,534,356 B2 * 5/2009 Saccomanno ............ 210/748.11
7,695,675 B2 * 4/2010 Kaiser et al. ..................... 422/24
2004/0045886 A1 * 3/2004 Abe et al. .................... 210/198.1
2005/0072449 A1 * 4/2005 Alpert et al. ................ 134/25.1
2005/0263716 A1 * 12/2005 From et al. ............... 250/453.11
2006/0108293 A1 * 5/2006 Brolin et al. .................. 210/748
2006/0186059 A1 * 8/2006 Saccomanno ................ 210/748
2006/0207431 A1 * 9/2006 Baca et al. ...................... 96/224
2008/0121812 A1 * 5/2008 Bircher ......................... 250/435
2008/0302735 A1 * 12/2008 Denkewicz et al. .......... 210/748

FOREIGN PATENT DOCUMENTS

CN        1929870 A    3/2007
JP      2003266088 A * 9/2003  ............... C02F 1/78

OTHER PUBLICATIONS

Apr. 15, 2013 Office Action for Canadian Patent Application No. 2,731,119.

(Continued)

*Primary Examiner* — Andrew Smyth
(74) *Attorney, Agent, or Firm* — Katten Muchin Rosenman LLP

(57) ABSTRACT

There is described a fluid treatment system in which fluid to be treated is impinged under pressure on a radiation emitting surface. The fluid treatment system includes at least one radiation source having a radiation emitting surface and at least one nozzle element having a fluid discharge opening spaced from the radiation emitting surface. The fluid discharge opening is configured to impinge fluid to be treated on to at least a portion of the radiation emitting surface. The fluid treatment system is well suited to treating low transmittance fluid.

23 Claims, 20 Drawing Sheets

(56) References Cited

OTHER PUBLICATIONS

The First Office Action for China Patent Application No. 200980138268.0 with a mailing date of Mar. 11, 2013.

International Search Report and Written Opinion of the International Searching Authority for International Application No. PCT/CA2009/000977, published as WO 2010/006428 A1.
May 16, 2012 Office Action for Canadian Patent Application No. 2,731,119.

* cited by examiner

FLUID TREATMENT SYSTEM

CROSS-REFERENCE TO RELATED APPLICATION

The present application claims the benefit under 35 U.S.C. §119(e) of provisional patent application Ser. No. 61/129,732, filed Jul. 15, 2008, and is a §371 of PCT/CA09/00977, filed Jul. 15, 2009, the contents of both of which are hereby incorporated by reference.

BACKGROUND OF THE INVENTION

1. Field of the Invention

In one of its aspects, the present invention relates to a fluid treatment system. In another of its aspects, the present invention relates to a process for treating fluid.

2. Description of the Prior Art

Mixing devices are known in the art and have been used to promote fluid turbulence—for example, to improve contact between elements in the flow path. Industrial applications of mixing are widely varied, and include heat exchange, reactor engineering and non-reactive blending.

One specific area of reactor engineering where mixing has been used is in the design of fluid treatment devices, particularly fluid radiation treatment devices. A specific such fluid radiation treatment device includes ultraviolet (UV) disinfection devices for water and wastewater treatment. The performance of UV disinfection devices depends, at least in part, on providing a prescribed dose of UV radiation to all fluid elements passing through (or otherwise being treated by) the device.

The UV dose received by a fluid element is defined as the product of UV intensity and exposure time. The accumulated UV dose received by a fluid element exiting the device is the sum of the individual doses received at each position. Since the UV intensity is attenuated with the distance from the UV source, it is desirable to mix fluid elements from regions far from the UV source to regions of higher intensity nearer to the source, thereby ensuring they receive an adequate dose of UV radiation. This type of mixing is particularly desirable when the transmittance of UV radiation through the fluid being treated is low (e.g., less than about 30% per cm), causing an increase in the attenuation of UV intensity with distance from the source—this is commonly encountered in UV disinfection devices for the treatment of liquids such as wastewater.

U.S. Pat. No. 5,846,437 [Whitby et al. (Whitby)], assigned to the assignee of the present application, teaches turbulent mixing in a UV system. More specifically, Whitby teaches the use of one or more ring-shaped devices (e.g., washers) at predetermined locations on the exterior surface of each lamp unit in the system and/or ring-shaped devices upstream of each lamp unit to increase turbulent mixing of fluid passing by the lamp units. While such ring-shaped devices as taught in Whitby are useful in increasing turbulence between the lamp units, the turbulent flow of fluid tends to be of a random or non-ordered (e.g., isotropic) nature.

In many systems, such as those where the mixing zone is longitudinal with respect to the direction of fluid flow therethrough, it is desirable to have plug flow in the flow direction and effective mixing in the transverse (to flow) direction. A specific or ordered pattern of fluid flow in the mixing zone is desirable (e.g., a "particle" of fluid oscillating toward and away from the lamp as it passes longitudinally with respect thereto), which is in contrast to general mixing in all directions (i.e., in contrast to random mixing or turbulence taught by Whitby). A longitudinal vortex is an example of this type of flow pattern. Vortices can be formed actively through energy input to the fluid, such as by employing a motorized fluid impeller.

Another means of achieving vortex generation is through the use of a passive element which is designed to cause the formation of the desired flow pattern (vortex generator).

U.S. Pat. Nos. 5,696,380, 5,866,910 and 5,994,705 [all in the name Cooke et al. (Cooke)] teach a flow-through photochemical reactor. The subject reactor taught by Cooke comprises an elongate annular channel in which is disposed an elongate radiation source. The channel includes static, fluid-dynamic elements for passively inducing substantial turbulent flow within the fluid as it passes through the channel. According to Cooke, each such static, fluid-dynamic element advantageously creates a pair of "tip vortices" in the fluid flow past each element. The "tip vortices" purportedly are counter-rotating about an axis parallel to the elongate annular chamber.

U.S. Pat. No. 6,015,229 [Cormack et al. (Cormack)], assigned to the assignee of the present application, teaches a fluid mixing device. The fluid mixing device comprises a series of "delta wing" mixing elements which cause the formation of vortices thereby improving fluid mixing. A specific embodiment of such a device illustrated in Cormack is the use of "delta wing" mixing elements to cause such vortex mixing between UV radiation sources in an array of such sources. This creates the potential for increasing distance between adjacent UV radiation sources in the array which, in turn, allows for a reduction in hydraulic head loss of the fluid flow through a UV disinfection system comprising the fluid mixing device.

U.S. Pat. No. 7,166,850 [Brunet et al. (Brunet)] teaches a fluid treatment device having at least one mixing element oriented in a manner to achieve improved mixing of the fluid. The fluid mixing device comprises at least one mixing element and is designed to create at least one vortex adjacent to a surface of the mixing device which is downstream of the mixing element. The mixing element comprises a centroid and is oriented in the fluid flow in a manner such that a first normal located at the centroid of the mixing element intersects a second normal emanating from the surface at the centroid of the mixing element such that the first normal, the second normal and the direction of fluid flow are in a non-planar relationship—see FIG. 2 of Brunet. This novel orientation of the mixing element results in improved fluid mixing. For example when the fluid mixing device is employed in a fluid treatment system such as UV disinfection system the improved fluid mixing is manifested in an improvement of UV dose delivery of the system. Additionally, in various preferred embodiments of the fluid mixing device taught by Brunet, such improved fluid mixing is accompanied by a reduction in hydraulic head loss of fluid passing through the system.

Despite the advances in the art made by Cooke, Cormack and Brunet, there is still room for improvement.

The systems taught by Cooke, Cormack and Brunet operate on the same general principle, namely that fluid is subject to some form of turbulence as it travels in a direction substantially parallel to the longitudinal axis of the elongate radiation source. The various mixing elements taught by Cooke, Cormack and Brunet create vortices and the like of varying degrees to optimize exposure of the fluid to radiation as the fluid travels in a direction substantially parallel to the longitudinal axis of the elongate radiation source. Unfortunately, for fluids having very low transmittance (e.g., transmittance less than 30% and as low as 5% or less), even with these enhanced mixing approaches, the fluid may not receive sufficient radiation to result in prescribed disinfection thereof.

SUMMARY OF THE INVENTION

It is an object of the present invention to obviate or mitigate at least one of the above-mentioned disadvantages of the prior art.

It is another object of the present invention to provide a novel fluid treatment system.

It is another object of the present invention to provide a novel process for treating a fluid.

Accordingly, in one of its aspects, the present invention provides a fluid treatment system comprising at least one radiation source having a radiation emitting surface and at least one nozzle element having a fluid discharge opening spaced from the radiation emitting surface, the fluid discharge opening being configured to impinge fluid to be treated on to at least a portion of the radiation emitting surface.

In another of its aspects, the present invention provides a fluid treatment system comprising:

a fluid inlet for receiving a pressurized flow of fluid;

a fluid treatment zone in fluid communication with the fluid inlet;

at least one elongate radiation source disposed in the fluid treatment zone;

a plurality of nozzle elements arranged in an annular configuration with respect to the elongate radiation source, each nozzle element having a fluid discharge opening configured to impinge fluid to be treated on to at least a portion of the elongate radiation source; and a fluid outlet for discharging treated fluid.

In another of its aspects, the present invention provides a process for treating a fluid in the present fluid treatment system comprising the steps of:

(i) feeding a fluid to the at least one nozzle element;

(ii) discharging the fluid through the fluid discharge opening in the at least one nozzle element;

(iii) impinging discharged fluid on to the radiation emitting surface; and (iv) exposing the fluid from Step (iii) to radiation.

Thus, the present inventors have discovered a fluid treatment system in which fluid to be treated is impinged under pressure on a radiation emitting surface. Generally, the specific design and optimization of the present fluid treatment system will depend on a combination of factors such as pressure drop, flow rate, nozzle size, nozzle shape, nozzle length, total nozzle open area in reactor, fluid velocity and the distance from the fluid discharge opening of the nozzle element to the radiation source. Preferably, the combination of these variables is balanced to ensure that a jet of fluid reaches the radiation source without requiring excessive pumping power while still having the correct flow pattern for optimal treatment. Greater distance from nozzle to the radiation source may result in the need for higher jet velocity. Higher fluid viscosity may also result in the need for higher jet velocity, since viscosity results in higher pressure drop through the nozzle and also rapid dissipation of the jet. Jet velocity can be increased, for a given flow rate, by decreasing the size of the fluid discharge opening, decreasing the total area of fluid discharge openings in a reactor and/or increasing the inlet flow rate. The exact relationships between nozzle size, viscosity, flow rate and pressure drop are known to those skilled in the art of fluid mechanics, and will not be described here in detail.

The present fluid treatment system is particularly well suited for treatment of fluid having a low transmittance—i.e., radiation transmittance expressed in %/cm (commonly also expressed simply as %). For example, the present fluid treatment system may be used to treat fluid having a transmittance of less than about 30% or less than about 25% or less than about 20% or less than about 15% or less than about 10% or less than about 5%. Thus, the transmittance of the fluid may be as low as about 0.0001% (an example of such a fluid would be milk) or 0.001% (an example of such a fluid would be animal waste stream such as fish waste stream). The actual transmittance of such low transmittances fluid may be determined using techniques within the purview of a person skill in the art—e.g., thin film techniques, dilution techniques and the like. It is possible for the transmittance of the fluid to be in a range using any combination of the above-mentioned lower limits and upper limits. When the radiation source is an ultraviolet radiation source, transmittance is known as UV transmittance or "UVT".

For all embodiments of the present fluid treatment system, it is preferred that the cross-sectional area of the fluid discharge opening in a given nozzle element be less than the cross-sectional area of the radiation emitting surface or the radiation source.

BRIEF DESCRIPTION OF THE DRAWING

Embodiments of the present invention will be described with reference to the accompanying drawings, wherein like reference numerals denote like parts, and in which.

DETAILED DESCRIPTION OF THE PREFERRED EMBODIMENTS

Figure 1:
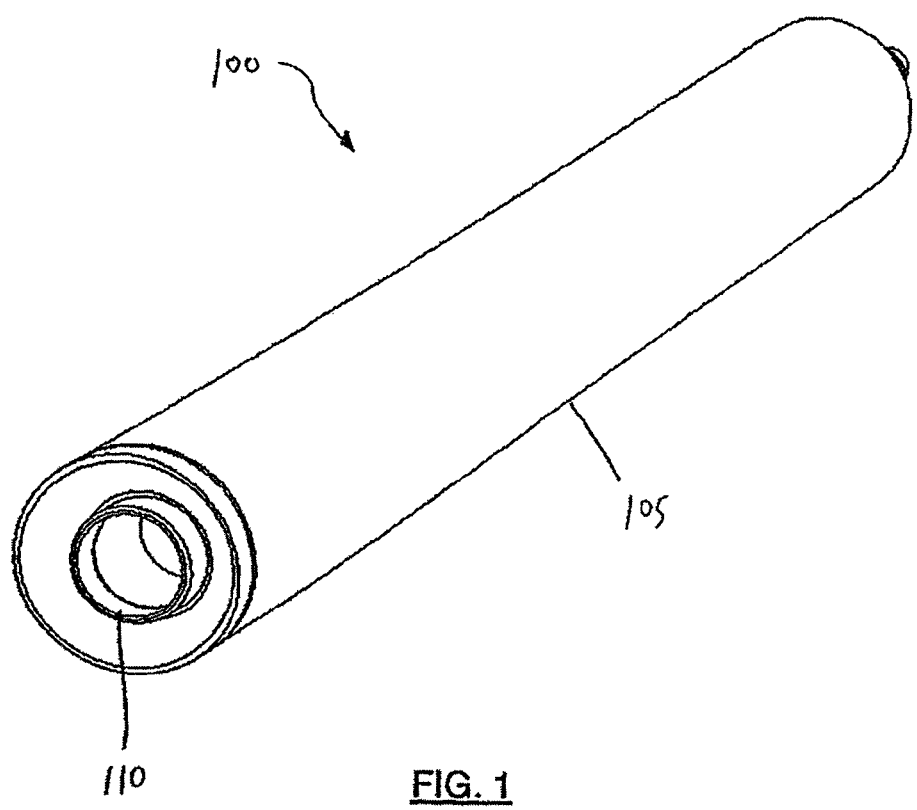
FIG. 1 illustrates the perspective view of a first embodiment of the outlet end of the present fluid treatment system.
Figure 2:
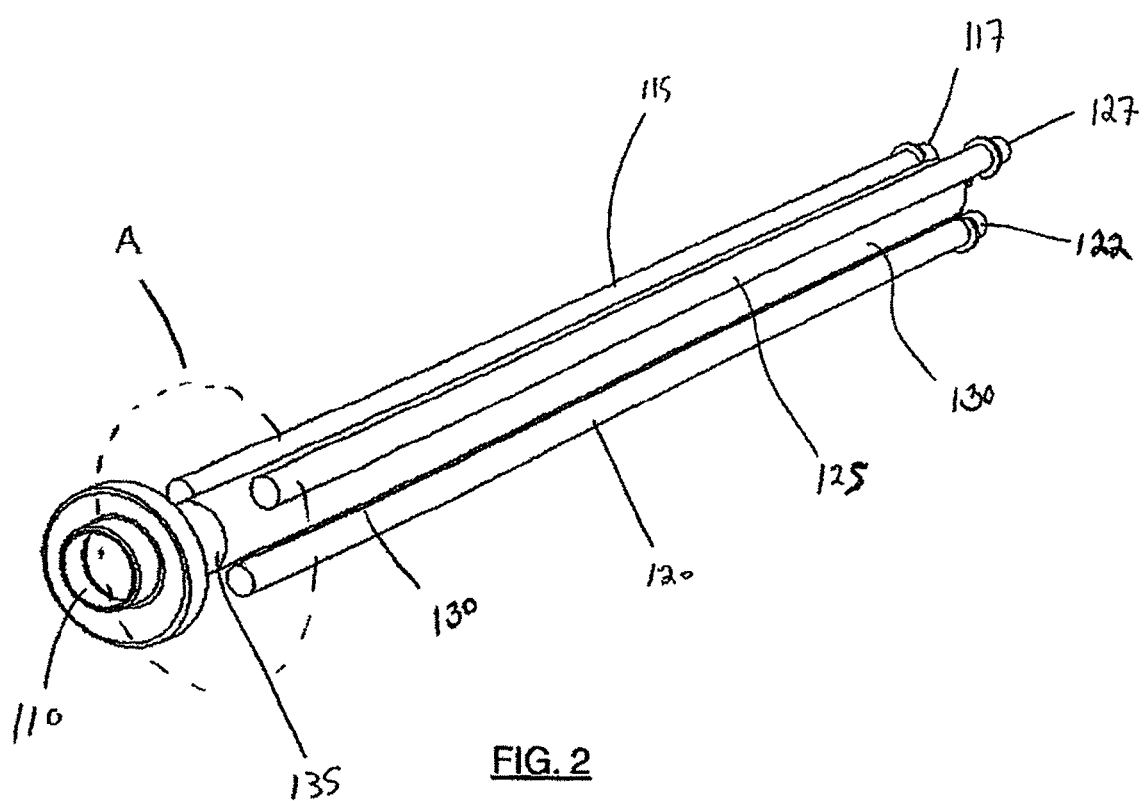
FIG. 2 illustrates a perspective, schematic view of the major internal components of the fluid treatment system illustrated in FIG. 1.
Figure 3:
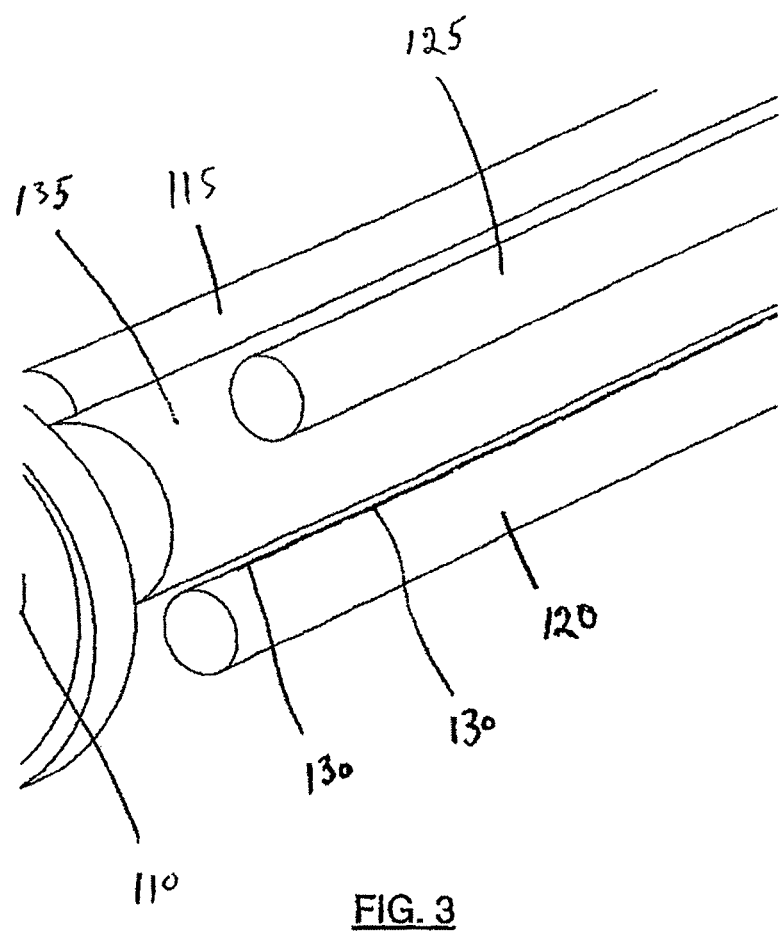
FIG. 3 illustrates an enlargement of portion A of FIG. 2.
Figure 4:
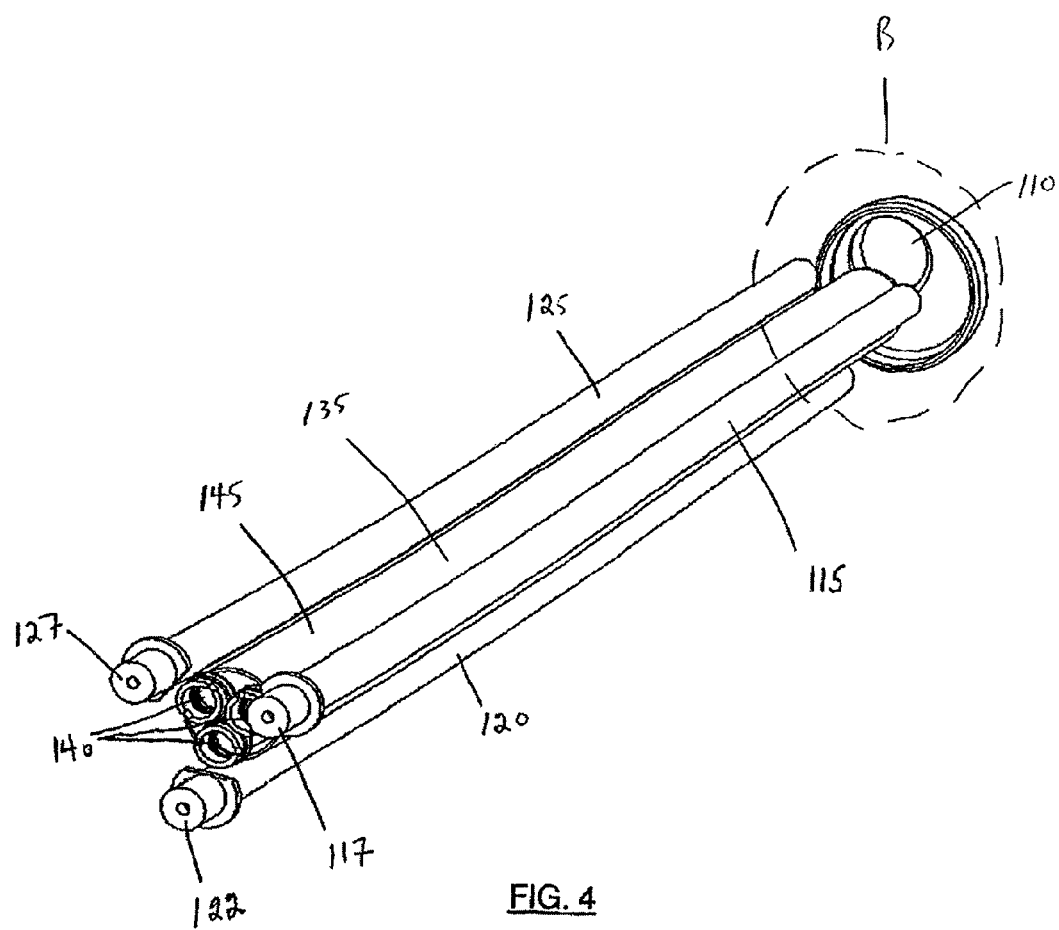
FIG. 4 illustrates a perspective, schematic view of the major internal components from the inlet end of the fluid treatment system illustrated in FIG. 1.
Figure 5:
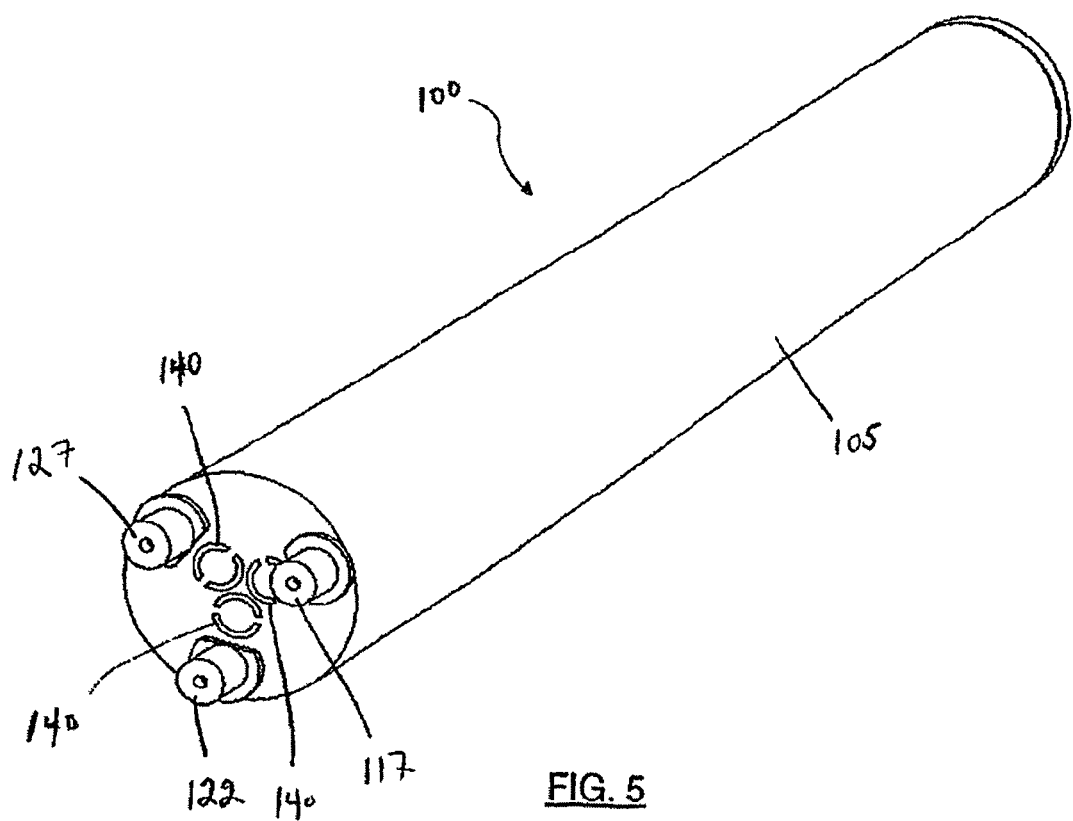
FIG. 5 illustrates a perspective view of the inlet end of the fluid treatment system illustrated in FIG. 1.
Figure 6:
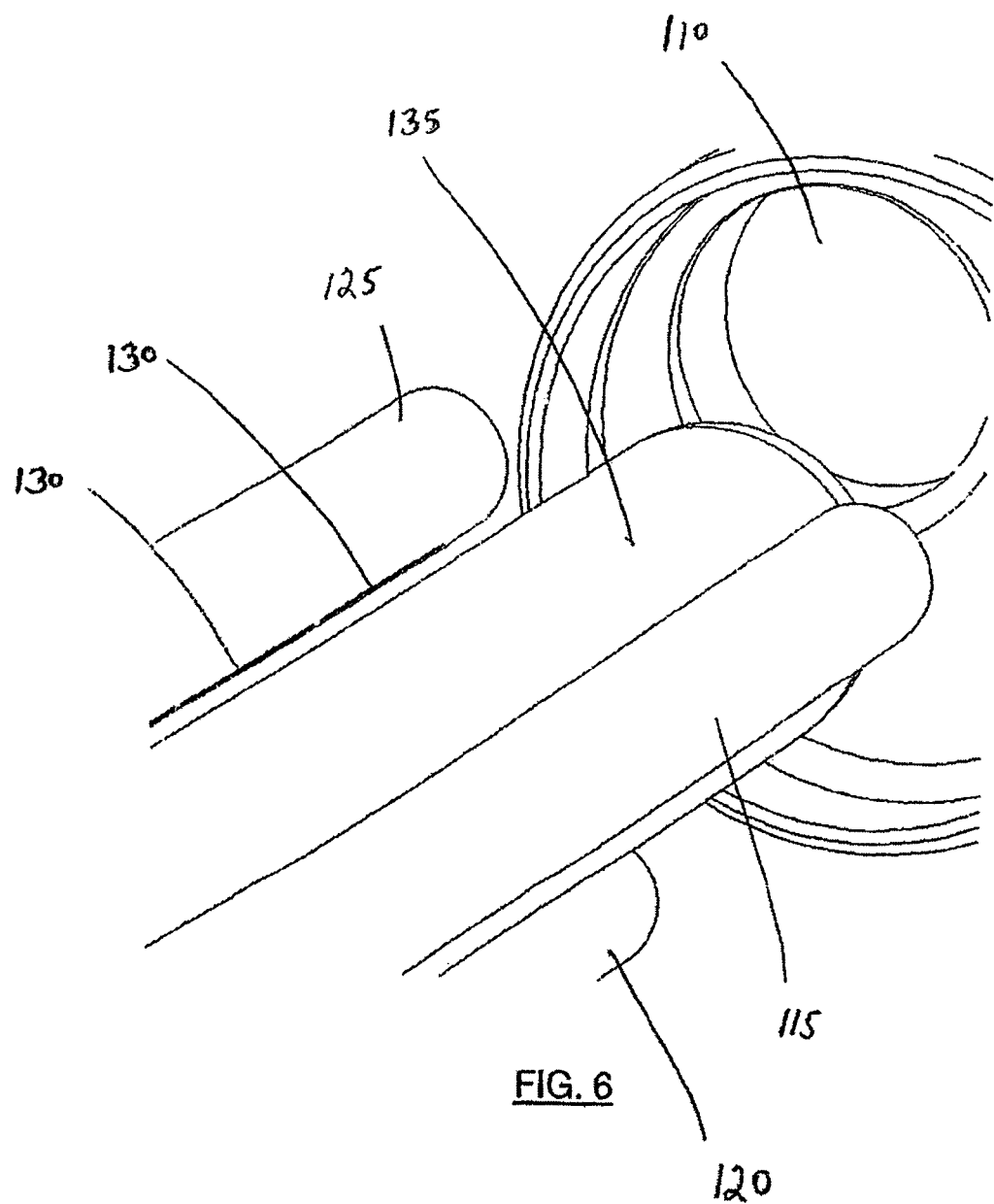
FIG. 6 illustrates an enlargement of portion B of FIG. 4.
Figure 7:
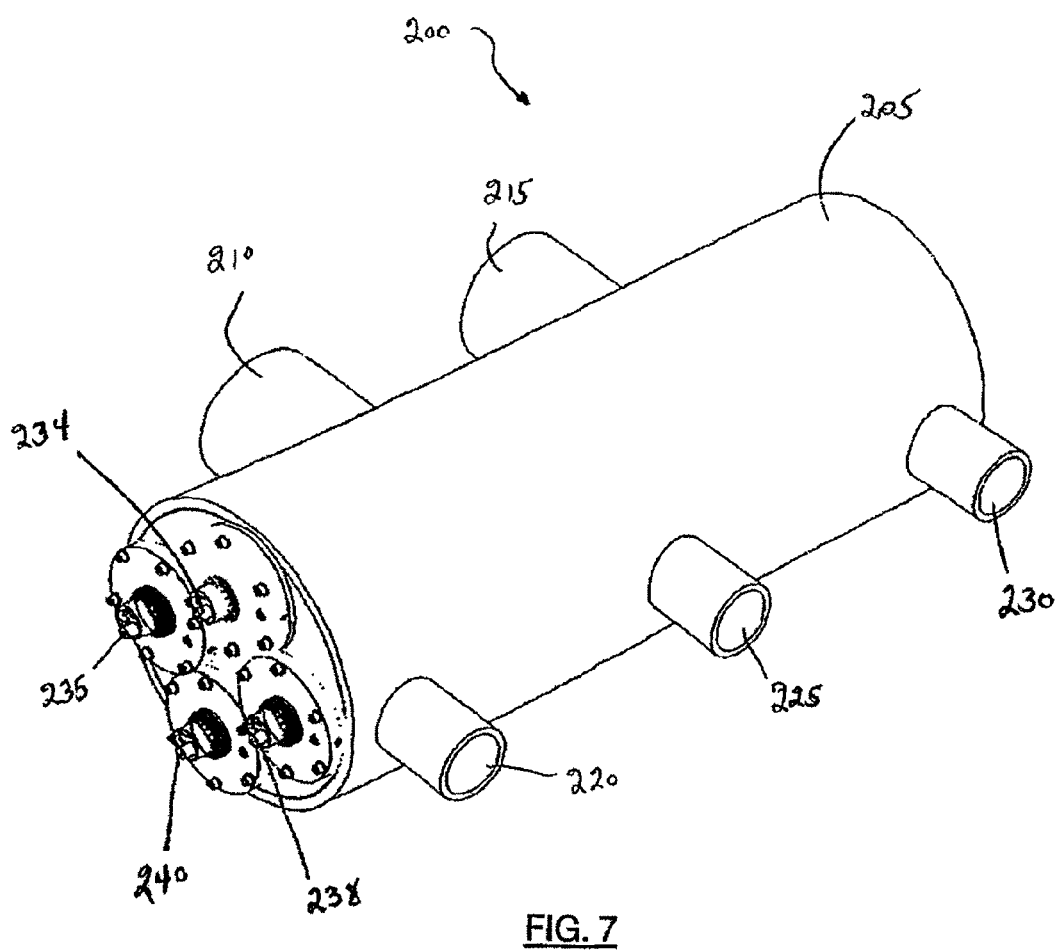
FIG. 7 illustrates a perspective view of a second embodiment of the present fluid treatment system.
Figure 8:
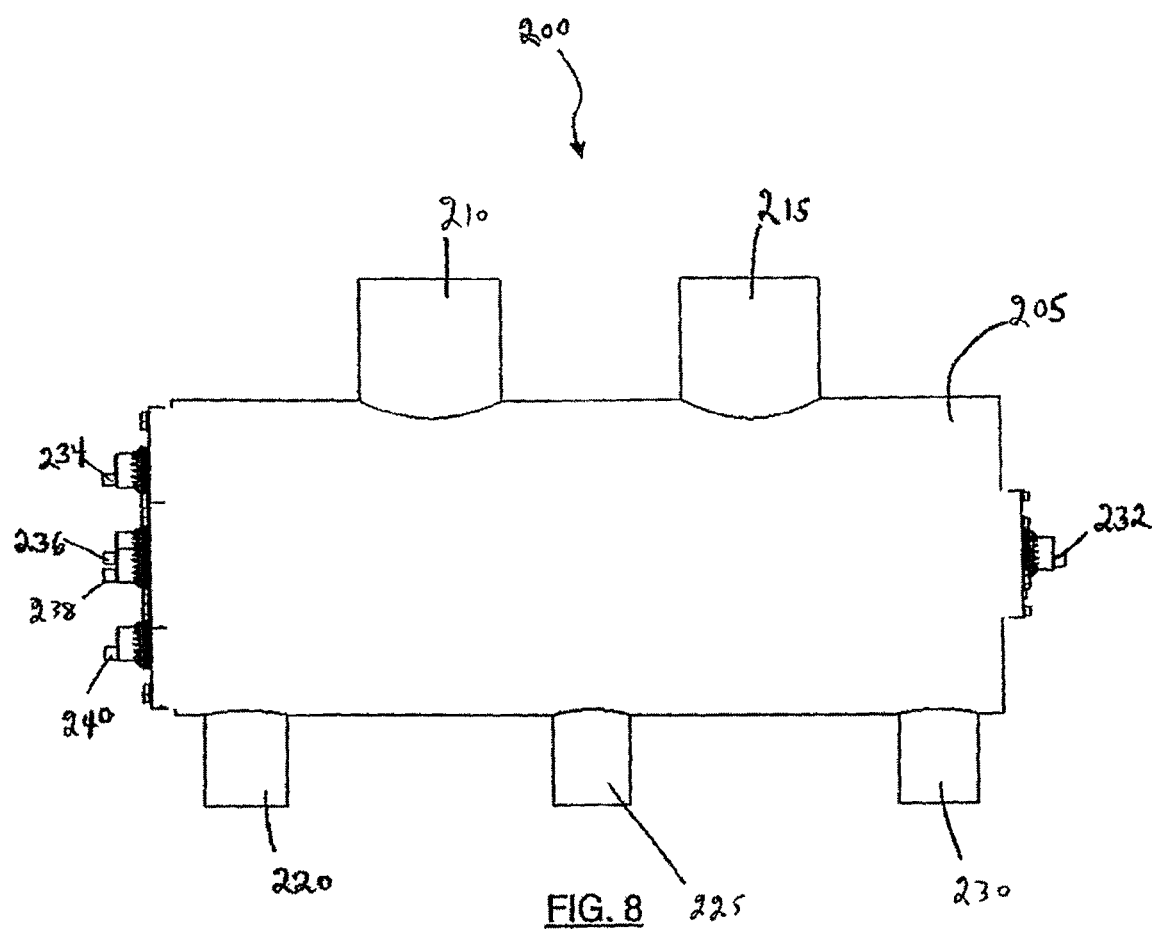
FIG. 8 illustrates a top view of the fluid treatment system illustrated in FIG. 7.

With reference to FIGS. 1-6, there is illustrated a fluid treatment system 100. Fluid treatment system 100 comprises a housing 105 having a fluid outlet 110. Disposed in housing 105 is a trio of pressurized nozzle elements 115,120,125. Nozzle elements 115,120,125 each comprises a pressurized fluid inlet 117,122,127, respectively. The manner in which fluid inlets 117,122,127 are connected to a supply of fluid is conventional.

Each of nozzle elements 115,120,125 comprises a series of elongate fluid discharge openings 130 that are disposed in a spaced manner along a longitudinal axis of nozzle elements 115,120,125.

Nozzle elements 115,120,125 are disposed in an annular configuration around a radiation source 135. In the illustrated embodiment (particularly, FIG. 4), radiation source 135 consists of a trio of radiation lamps 140 disposed in a single quartz sleeve 145. As will be appreciated by those of skill in the art, quartz sleeve 145 comprises a radiation emitting surface once radiation lamps 140 have been actuated. Preferably, lamps 140 are ultraviolet radiation lamps (e.g., Low Pressure High Output (LPHO) lamps, amalgam lamps, medium pressure lamps, light emitting diode (LED) radiation sources and the like). If radiation source 135 is a Dielectric Barrier Discharge (DBD) lamp it is possible, in some cases, to utilize the lamp without the need for a protective sleeve. Such lamps are conventional in the art. While the illustrated embodiment shows a trio of radiation lamps 140 it is possible to use a bundle of 4 or more lamps or as few as a single radiation lamp 140 disposed in quartz sleeve 145.

For additional information on DBD lamps, reference may be made to one or more of:
International Publication Number 2007/071042, published Jun. 28, 2008 [Fraser et al.];
International Publication Number 2007/071043, published Jun. 28, 2008 [Fraser et al.]; and
International Publication Number 2007/071074, published Jun. 28, 2008 [Fraser et al.].

For additional information on LED radiation sources, reference may be made to International patent application S.N. PCT/CA2008/001036, filed Jun. 2, 2008 (Knight et al.).

With respect to the radiation source useful in the present fluid treatment system, those of skill in the art, having the present specification in hand, will understand it is possible to utilize a radiation source which is a beam source or a point source.

Those of skill in the art, having the present specification in hand, will understand it is possible to optimize the distance between fluid discharge openings 130 and quartz sleeve 145 (or other radiation emitting surface). For example, at a given fluid pressure, as the transmittance of the fluid being treated goes down, it is possible to optimize fluid treatment by moving fluid discharge openings 130 closer to quartz sleeve 145 and/or decreasing the cross-sectional size of fluid discharge openings 130 in order to increase the velocity to facilitate the fluid impacting quartz sleeve(s) 145.

In use, pressurized fluid is fed into each of nozzle elements 115,120,125. Preferably, the fluid is a liquid. As used throughout this specification, the term "liquid" is intended to have a broad meaning and is intended to encompass any composition of matter that is flowable at ambient or modified temperature and pressure. Preferably, the liquid is an aqueous liquid. For example, the fluid may be water or a foodstuff such as milk. The fluid may have a transmittance of less than about 30%. In some embodiments, the fluid may have an even lower transmittance—e.g. less than about 25%, less than about 20%, less than about 15%, less than about 10%, less than about 5%.

Given that the fluid in nozzle elements 115,120,125 is pressurized, it is discharged from fluid discharge openings 130 at a force which causes it to impinge on quartz sleeve 145 of radiation source 135. Preferably, the fluid discharge opening is spaced from quartz sleeve 145 to impinge fluid along a pathway that it is within about 45°, more preferably within about 30°, more preferably within about 20°, more preferably within about 15°, more preferably within about 10°, more preferably within about 5° with respect to a normal to a contact point of a tangent to quartz sleeve 145. In a highly preferred embodiment, the fluid discharge opening is spaced from quartz sleeve 145 to impinge fluid along a pathway that is substantially normal to a tangent quartz sleeve 145.

In the illustrated embodiments, the annular arrangement of nozzle elements 115,120,125 causes fluid to be impinged on most of the surface of quartz sleeve 145. Of course it is possible to use more or fewer than three nozzle elements.

With reference to FIGS. 7-13, there is illustrated a fluid treatment system 200. Fluid treatment system 200 comprises a housing 205 having a pair of inlets 210,215 and a trio of outlets 220,225,230. Connected to one end of housing 205 is one radiation source assembly 232. Connected to the other end of housing 205 are four radiation source assemblies 234, 236,238,240. Each of radiation source assemblies 232,234, 236,238,240 comprises a radiation lamp as discussed above with reference to fluid treatment system 100 illustrated in FIGS. 1-6—e.g., an ultraviolet radiation lamp disposed within a quartz sleeve.

Each of the radiation source assemblies is disposed in a jet bundle 245 which will be discussed in more detail below.

Figure 9:
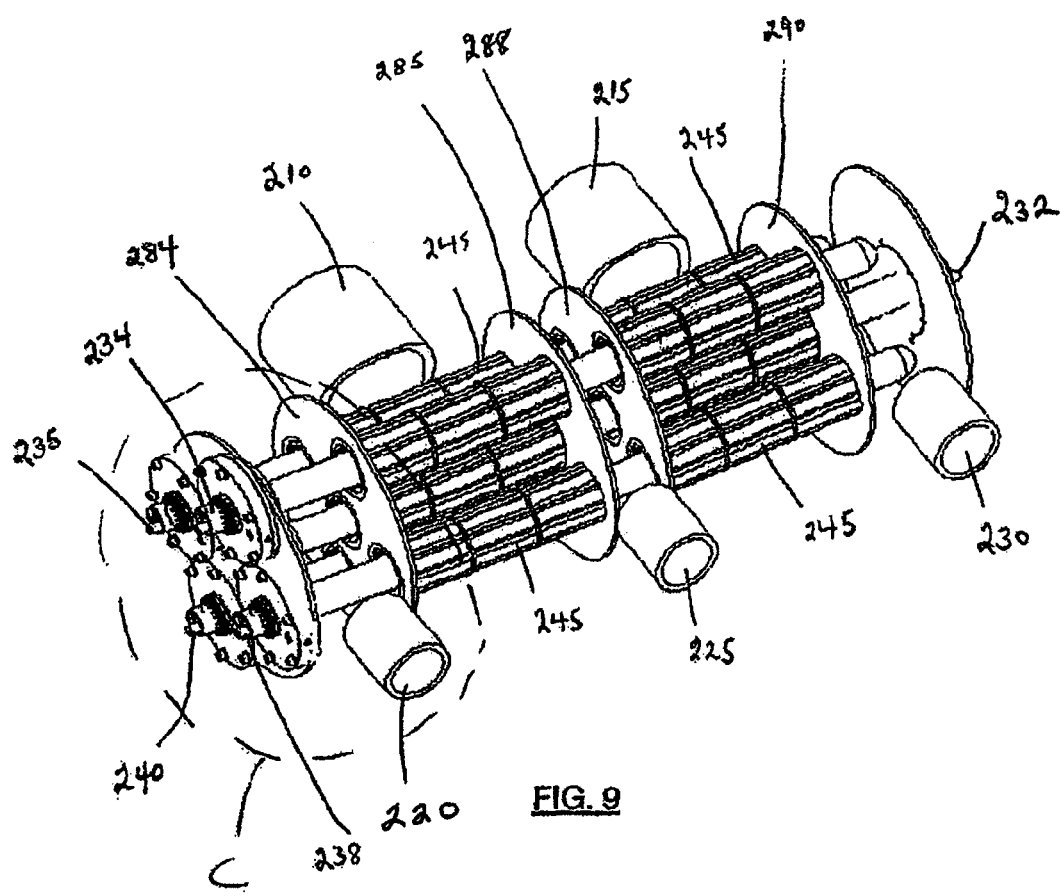
FIG. 9 illustrates a perspective, schematic view of the internal components of the fluid treatment system illustrated in FIG. 7.
Figure 10:
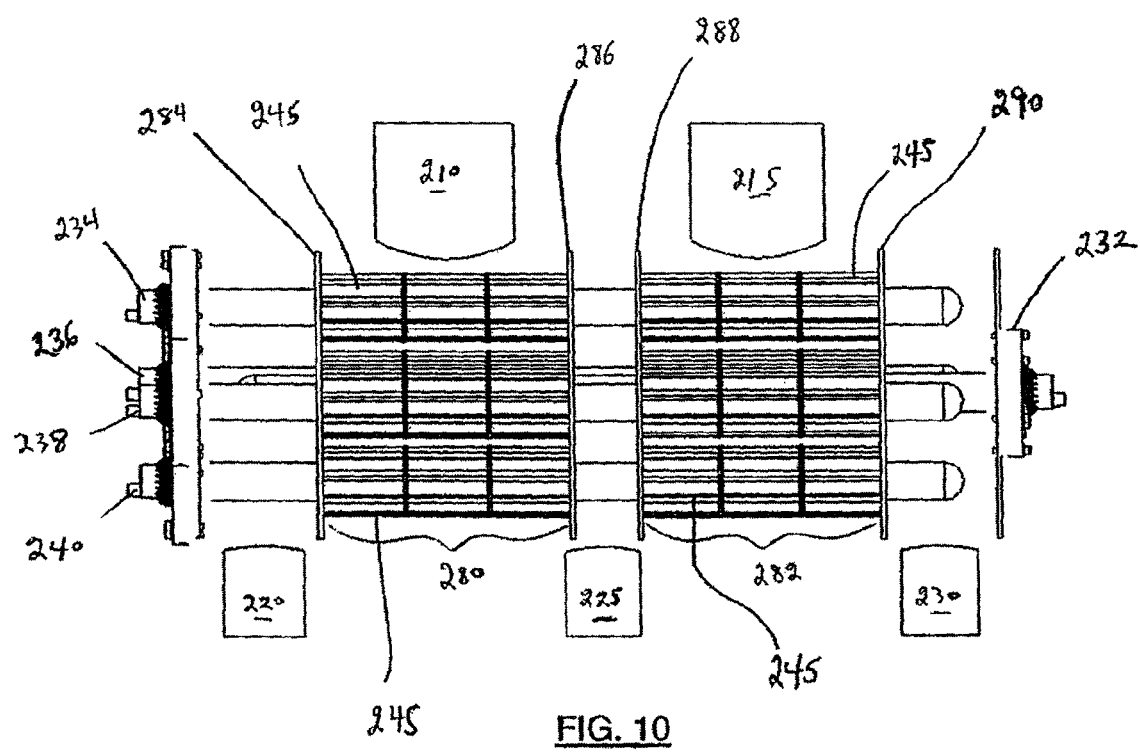
FIG. 10 illustrates a top, schematic view of the internal components of the fluid treatment system illustrated in FIG. 8.
Figure 11:
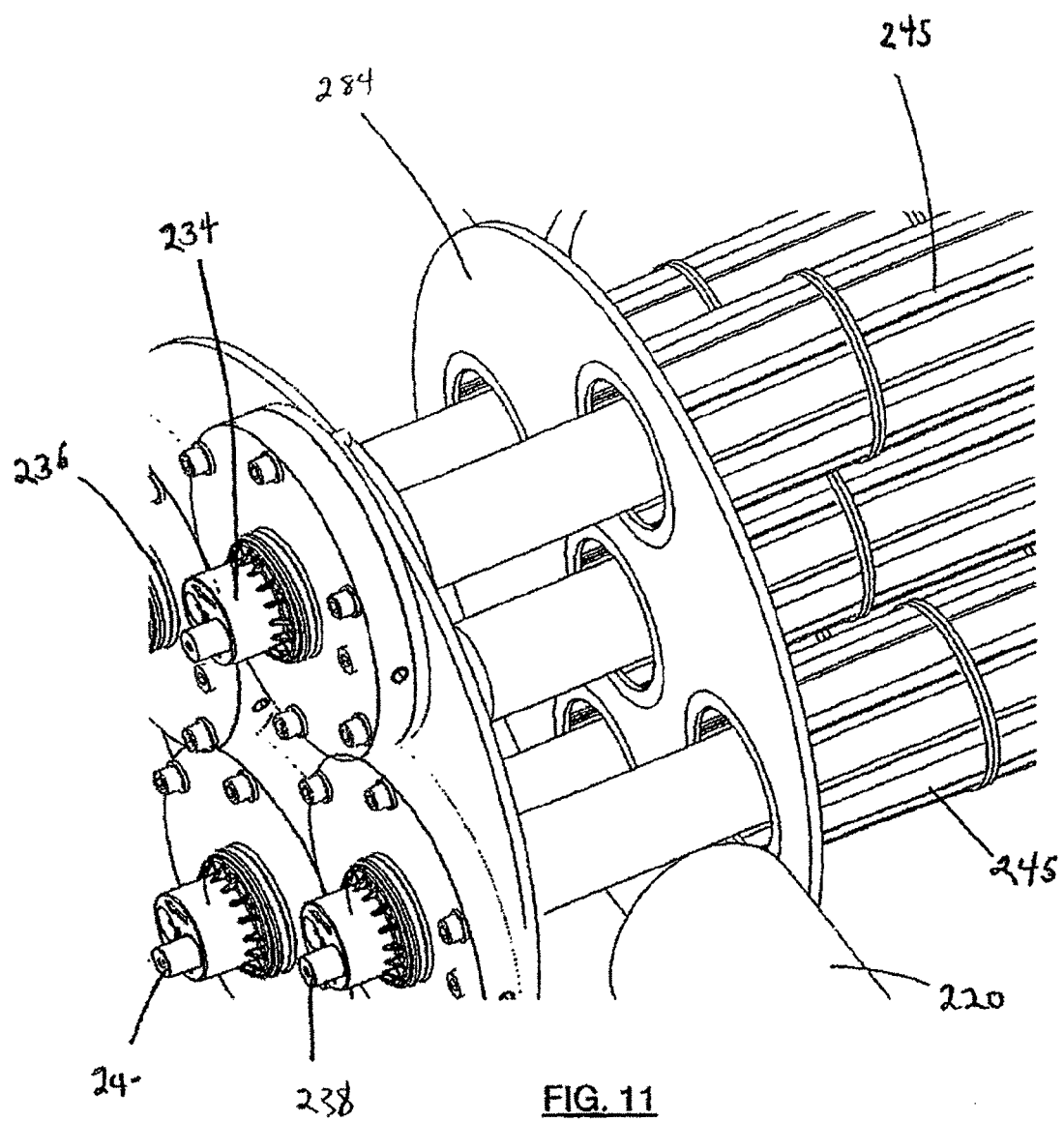
FIG. 11 illustrates an enlarged view of portion C in FIG. 9.

With particular reference to FIGS. 9 and 10, the interior of housing 205 is divided into a first sub-chamber 280 and a second sub-chamber 282. These subchambers are divided through the use of pressure plates 284,286,288,290. By selecting appropriate dimensions in the openings in pressure plates 284,286,288,290, it is possible to create two flow paths through housing 205. The first flow path involves pressurized fluid passing through inlet 210, subchamber 280 and being discharged through outlets 220,225. The second flow path involves pressurized fluid passing through inlet 215, subchamber 282 and being discharged through outlets 225,230.

Of course, those of ordinary skill in the art will recognize that it is not necessary to use sub-chambers 280,282. It is possible to construct a system which has a single chamber in the interior housing 205. Further, it is possible to design a system which uses more than two sub-chambers in the interior of housing 205.

Figure 12:
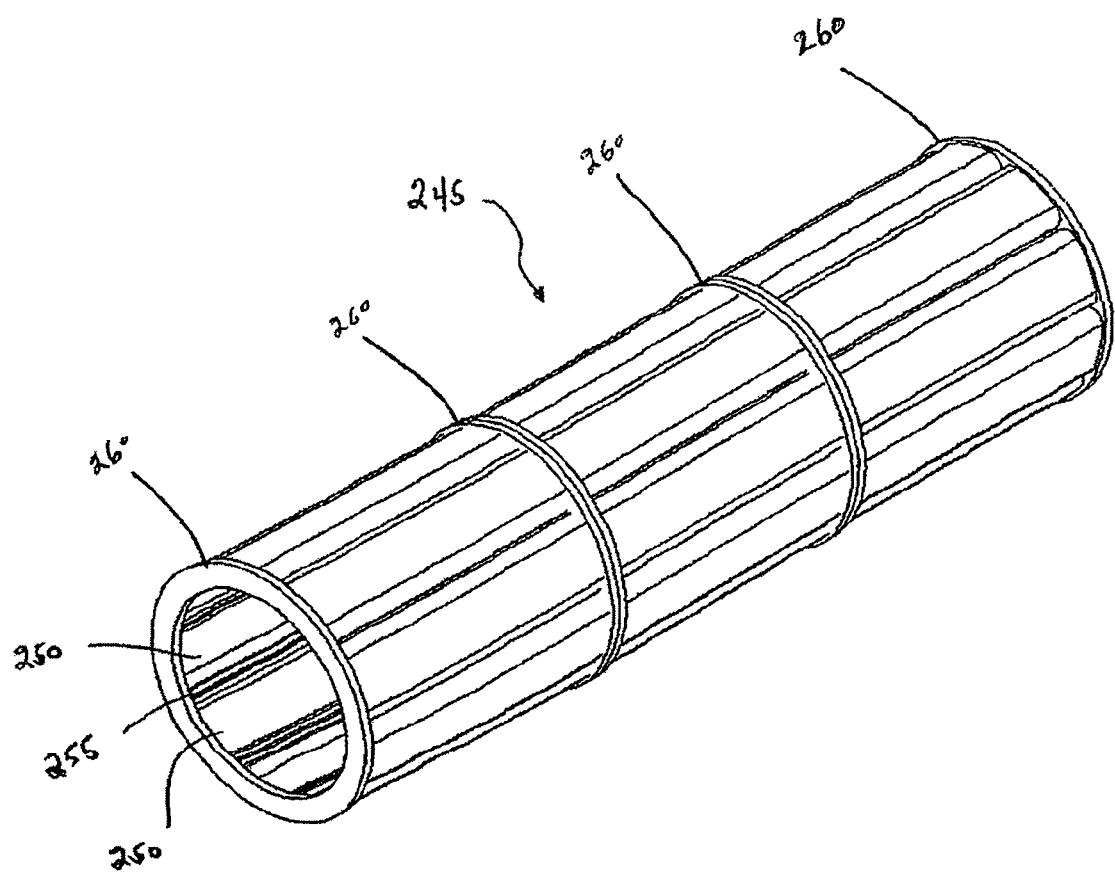
FIG. 12 illustrates an enlarged, perspective view of a single bundle of nozzle elements used in the fluid treatment system illustrated in FIGS. 8-11.
Figure 13:
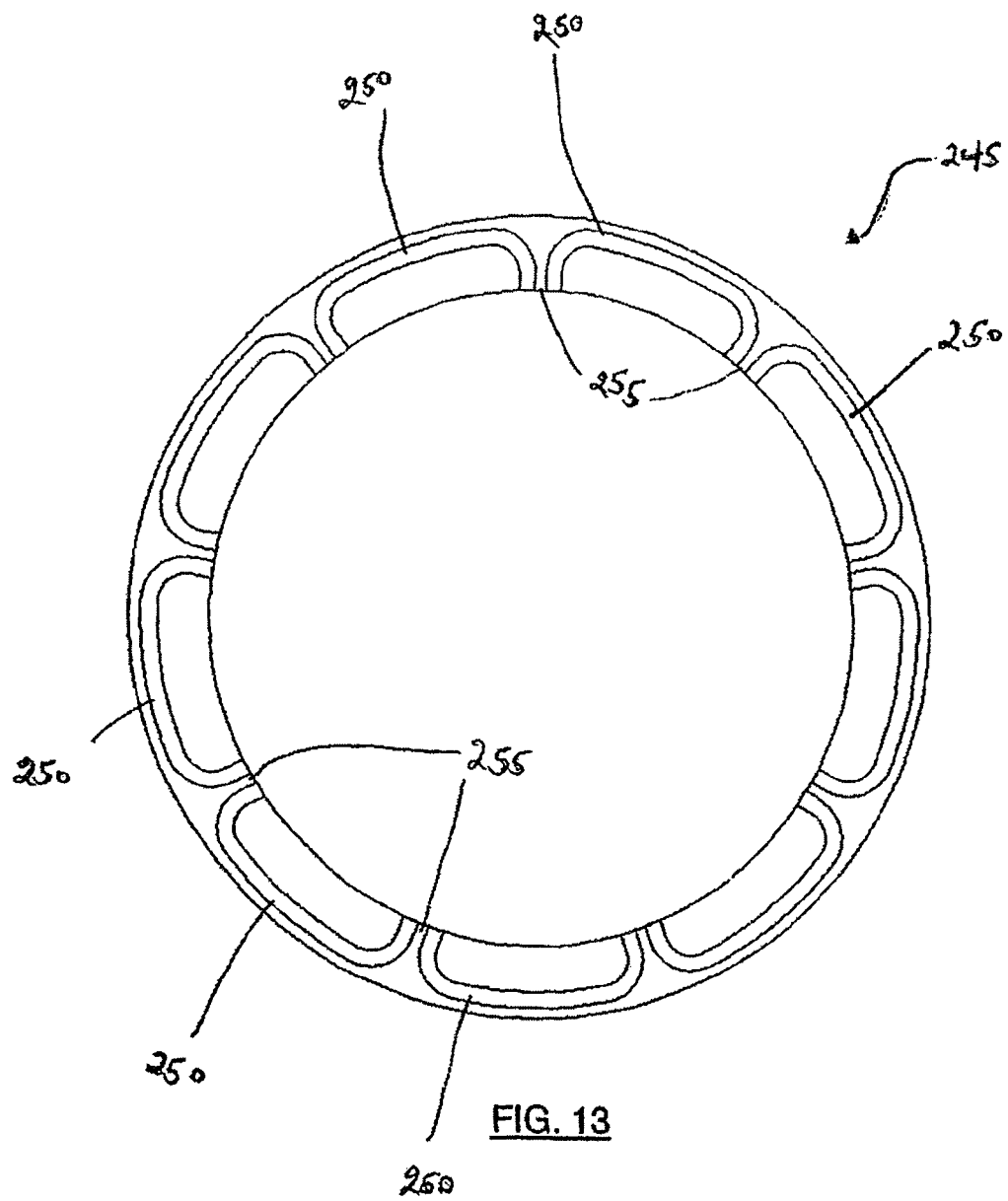
FIG. 13 illustrates a cross sectional view of the nozzle bundle illustrated in FIG. 12.

With particular reference to FIGS. 12 and 13, it will be seen that jet bundle 245 (shown without the radiation source assembly disposed therein) consists a number of plate elements 250 that are disposed in a spaced relationship with respect to one another to define a series of fluid discharge openings 255. A series of rings 260 serves to retain plate elements 250 in spaced relation with respect to one another.

In use, pressurized fluid is fed to inlets 210,215. This serves to pressurize the interior of housing 205. The pressurized fluid environment of the interior of housing 205 causes fluid to be discharged through fluid discharge openings 255 in jet bundles 245 so as to impinge on the quartz sleeve of radiation source assemblies 232,234,236,238,240. As the fluid impinges on the quartz sleeve, it is exposed to radiation and treated (e.g., disinfected). The treated fluid then exits outlets 220,225,230.

Figure 14:
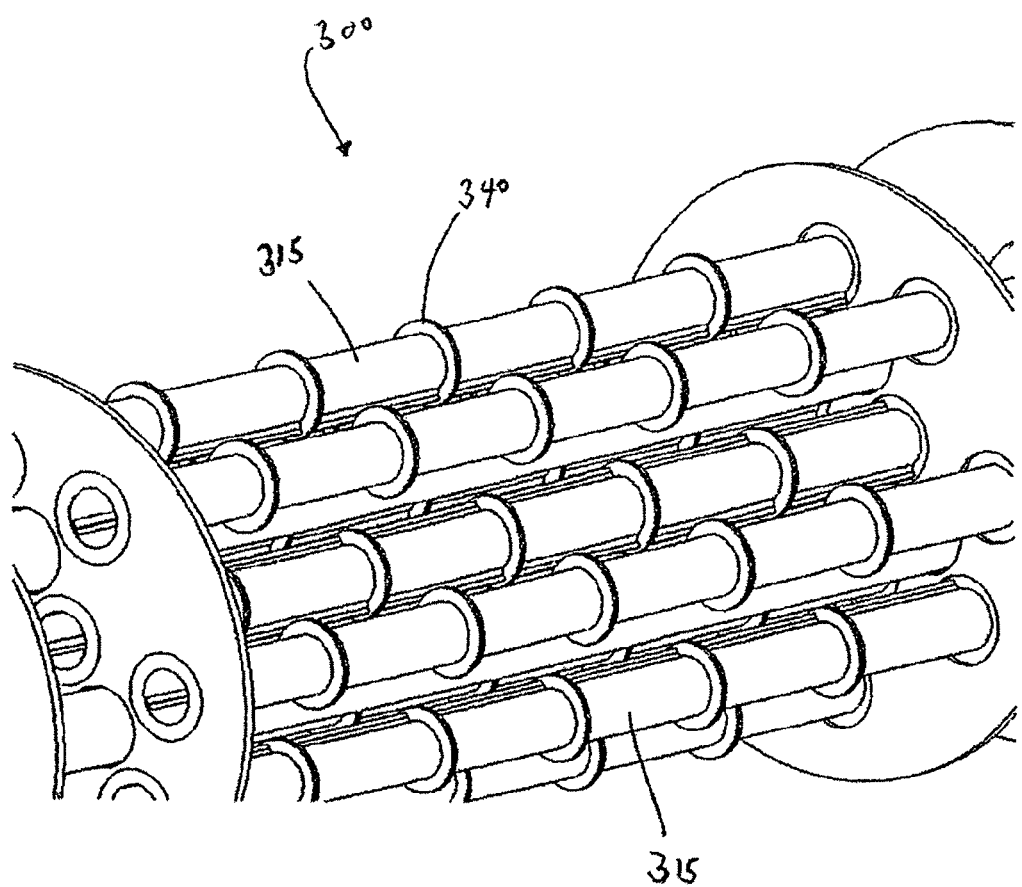
FIG. 14 illustrates a perspective, schematic view of the major internal components of a third embodiment of the present fluid treatment system.
Figure 15:
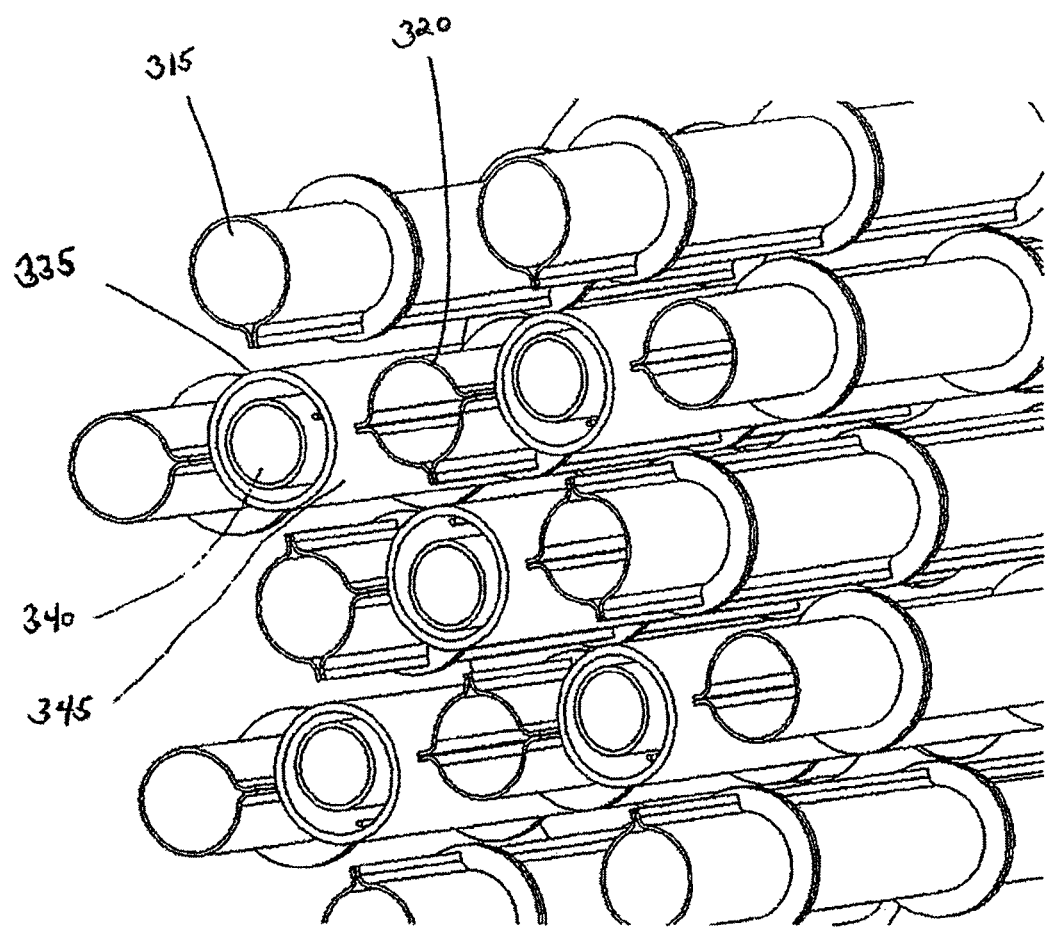
FIG. 15 illustrates a cut away perspective view of the embodiment of the present fluid treatment system illustrated in FIG. 14.
Figure 16:
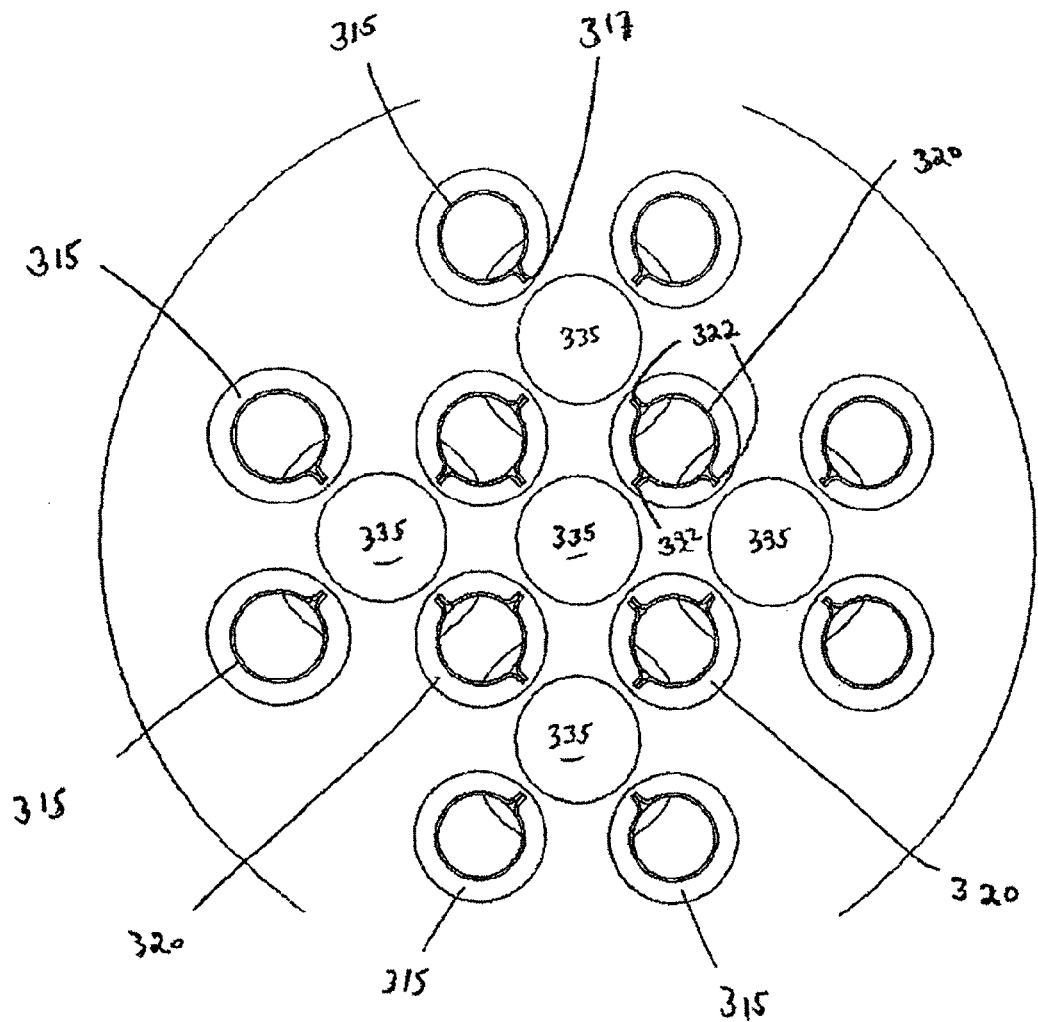
FIG. 16 illustrates an end view of the components of the fluid treatment system illustrated in FIG. 14.
Figure 17:
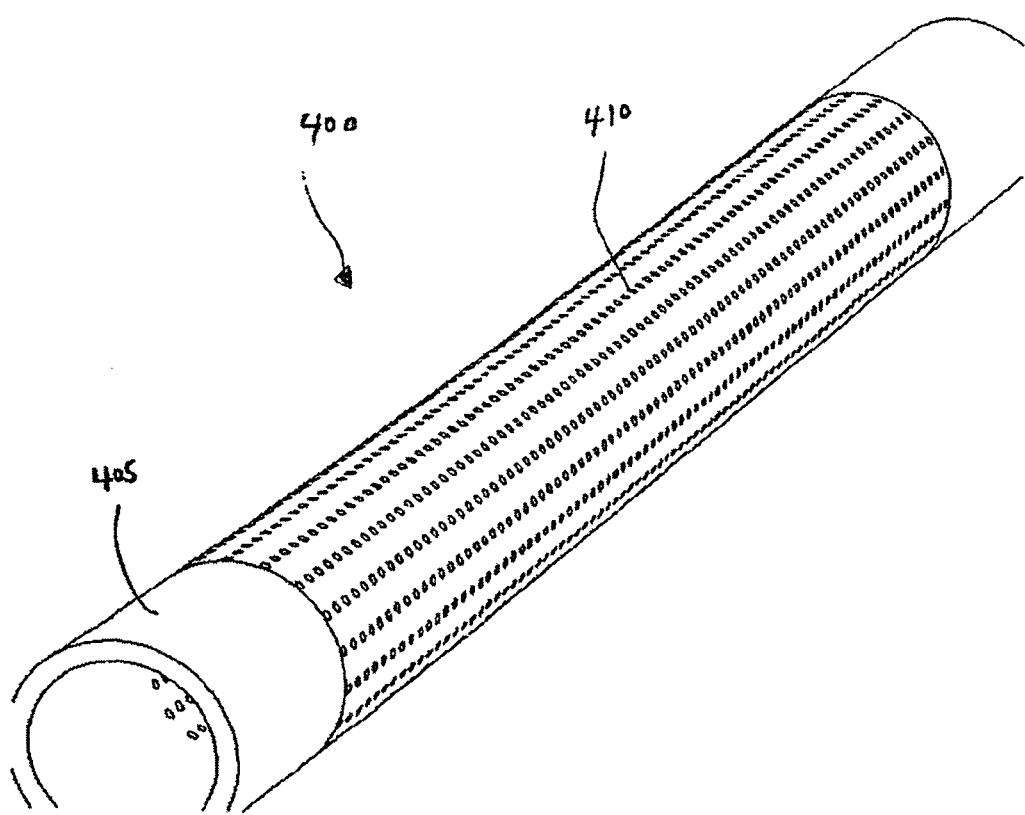
FIGS. 17-20 illustrate various views of a fluid pressure tube which may be used as an alternate to the nozzle bundle used in the embodiment of the invention illustrated in FIGS. 7-13.
Figure 18:
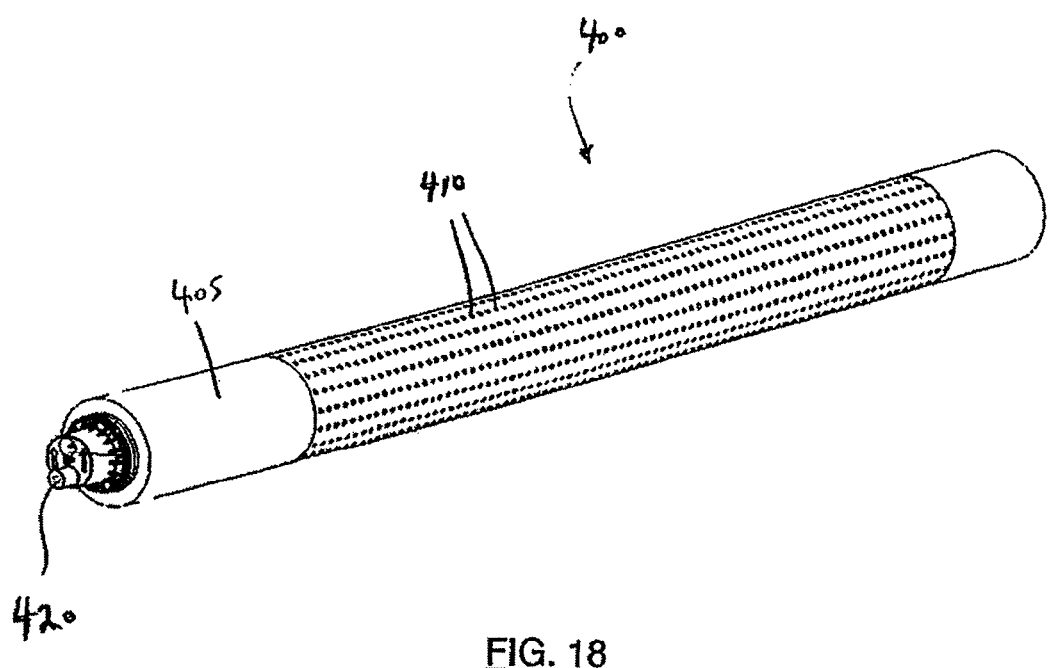
Figure 19:
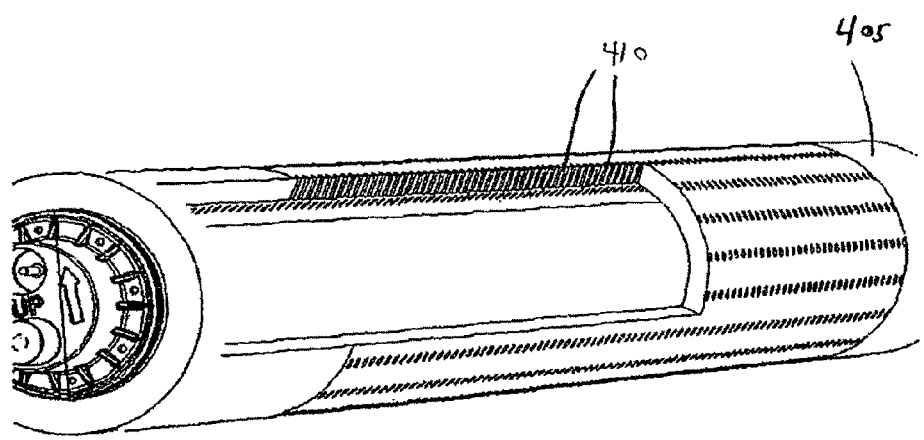
Figure 20:
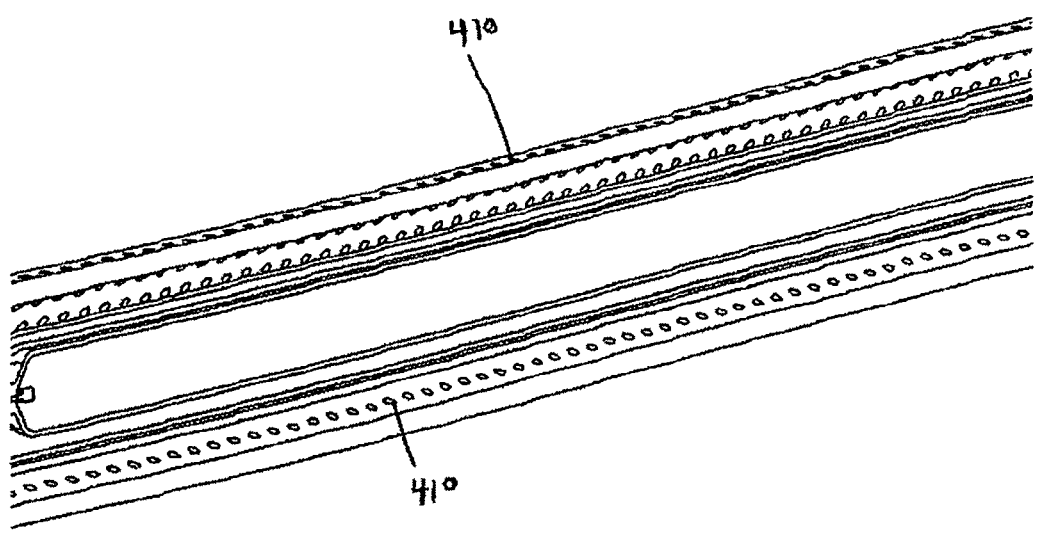

With reference to FIGS. 14-16, there is shown the internals of a fluid treatment system 300. Fluid treatment system 300 is similar to fluid treatment system 100 shown with respect to FIGS. 1-6 inasmuch as it utilizes a series of nozzle elements 315,320 which are disposed in a annular configuration around a radiation source 335 that consists of a radiation lamp 340 disposed in a radiation transparent sleeve 345.

Each of nozzle elements 315 includes an elongate opening 317 that is aligned with a longitudinal axis of radiation transparent sleeve 345. With particular reference to FIG. 16, nozzle element 320 contains a trio of elongate fluid discharge openings 322 since this nozzle element is capable of "seeing" three radiation sources 335. Each of nozzle elements 315,320 contains a series of retaining rings 340 which help stiffen and maintain the integrity of nozzle elements 315,320.

As will be appreciated by those of skill in the art, having the present specification in hand, it is possible to alter this arrangement so that the opening in the nozzle elements is not necessarily aligned with a longitudinal axis of the radiation transparent sleeve. For example, the opening could be spiral-shaped. It is preferred, however, that the nozzle elements be oriented to direct fluid in a direction substantially normal to the radiation source.

The operation of fluid treatment system 300 is similar to that described above with respect to fluid treatment system 100 in FIGS. 1-6.

With reference to FIGS. 17-20, there is illustrated a pressure tube 400 that can be used to replace jet bundle 245 in fluid treatment system 200 discussed above with reference to FIGS. 7-13. Pressure tube 400 comprises a tubular element 405 having disposed therein a series of openings 410. A radiation source assembly 420 is disposed in the interior of tubular member 405. Radiation source assembly 420 consists the radiation source and a radiation transparent sleeve.

The shape of fluid discharge openings 410 and their arrangement can be varied depending on factors such as the number of radiation sources disposed within tubular element 405, the distance between the radiation source(s) and tubular element 405, the pressure of fluid passing through fluid discharge openings 410 and the like (see above discussion under Summary of the Invention).

The illustrated embodiments are quite specific. It is possible to vary a number of features in these embodiments. These variable features are described in claims 1-148 which are hereby incorporated by reference to this description of the preferred embodiments of the present invention.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. In one possible alternative, it is possible (and even preferable in some cases) to periodically replace the fluid being treated with a cleaning agent. When the fluid treatment system is operated in this mode, the cleaning agent is impinged on the radiation emitting surface of the radiation source thereby removing accumulated fouling materials. The illustrated embodiments utilize a static nozzle element (static fluid discharge openings). In practice, in another possible alternative, it is possible to utilize a dynamic nozzle element and/or a nozzle element equipped with one or more variable fluid discharge openings—see one or more of U.S. Pat. No. 6,502,434, U.S. Pat. No. 6,279,839, U.S. Pat. No. 5,070,628 and U.S. Pat. No. 4,313,572. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A fluid treatment system comprising:
   a fluid inlet for receiving a pressurized flow of fluid;
   a fluid treatment zone in fluid communication with the fluid inlet;
   at least one elongate radiation source disposed in the fluid treatment zone;
   a plurality of nozzle elements arranged in an annular configuration with respect to the at least one elongate radiation source, each nozzle element having a fluid discharge opening configured to impinge fluid to be treated substantially axially with respect to an axis of the at least one elongate radiation source, the annular configuration of the plurality of nozzle elements being disposed so as to impinge the fluid to be treated substantially axially on to greater than one half of the entire length of a radiation emitting portion of the at least one elongate radiation source; and
   a fluid outlet for discharging treated fluid.

2. The fluid treatment system defined in claim 1, wherein the radiation source comprises a curved radiation emitting surface.

3. The fluid treatment system defined in claim 2, wherein the fluid discharge opening is spaced from the radiation emitting surface to impinge fluid along a pathway that is within about 45° with respect to a normal to a contact point of a tangent to the radiation emitting surface.

4. The fluid treatment system defined in claim 2, wherein the fluid discharge opening is spaced from the radiation emitting surface to impinge fluid along a pathway that is within about 10° with respect to a normal to a contact point of a tangent to the radiation emitting surface.

5. The fluid treatment system defined in claim 2, wherein the fluid discharge opening is spaced from the radiation emitting surface to impinge fluid along a pathway that is substantially normal to a contact point of a tangent to the radiation surface.

6. The fluid treatment system defined in claim 1, wherein the fluid discharge opening comprises a rectilinear shape.

7. The fluid treatment system defined in claim 1, wherein the fluid discharge opening comprises a curvilinear shape.

8. The fluid treatment system defined in claim 1, wherein the fluid discharge opening comprises a circular shape.

9. The fluid treatment system defined in claim 1, wherein the fluid discharge opening comprises a semi-circular shape.

10. The fluid treatment system defined in claim 1, wherein the plurality of nozzle elements is comprised in a container element.

11. The fluid treatment system defined in claim 10, wherein the container element is elongate and comprises a plurality of fluid discharge openings disposed along a longitudinal axis of the container element.

12. The fluid treatment system defined in claim 10, wherein the container element comprises an inlet for receiving a pressurized flow of fluid.

13. The fluid treatment system defined in claim 10, comprising a plurality of container elements spaced from the radiation emitting surface.

14. The fluid treatment system defined in claim 13, wherein the plurality of container elements is arranged annularly with respect to the radiation emitting surface.

15. The fluid treatment system defined in claim 1, wherein the plurality of nozzle elements comprises a plurality of fluid directing elements arranged in a spaced relationship to define a plurality of fluid discharge openings.

16. The fluid treatment system defined in claim 15, comprising the same number of fluid directing elements and fluid discharge openings.

17. The fluid treatment system defined in claim 15, further comprising a plurality of retaining elements for maintaining the fluid directing elements in the spaced relationship.

18. The fluid treatment system defined in claim 15, wherein the plurality of fluid directing elements are arranged to define an annular configuration around a central portion in which the at least one radiation source is disposed.

19. The fluid treatment system defined in claim 18, wherein a single radiation source is disposed coaxially with respect to the plurality of fluid directing elements.

20. The fluid treatment system defined in claim 18, comprising a plurality of the annular configurations.

21. The fluid treatment system defined in claim 1, comprising a plurality of fluid inlets and a plurality of fluid outlets.

22. The fluid treatment system defined in claim 21, wherein the fluid treatment zone comprises two or more subchambers, each subchamber in fluid communication with at least one fluid inlet and at least one fluid outlet.

23. The fluid treatment system defined in claim 22, wherein each subchamber is in fluid communication with a plurality of fluid inlets and a plurality of fluid outlets.

* * * * *